(12) United States Patent
Takeda (10) Patent No.: US 8,248,604 B2
(45) Date of Patent: Aug. 21, 2012

(54) FLOW CYTOMETER AND FLOW CELL FOR THE SAME

(75) Inventor: Kazuo Takeda, Mitaka (JP)

(73) Assignee: On-Chip Biotechnologies Co., Ltd, Tokyo (JP)

( * ) Notice: Subject to any disclaimer, the term of this patent is extended or adjusted under 35 U.S.C. 154(b) by 208 days.

(21) Appl. No.: 12/566,417

(22) Filed: Sep. 24, 2009

(65) Prior Publication Data
US 2011/0069311 A1    Mar. 24, 2011

(51) Int. Cl.
*G01N 21/00* (2006.01)
(52) U.S. Cl. .................................... 356/337; 356/338
(58) Field of Classification Search ........... 356/336–342
See application file for complete search history.

(56) References Cited

U.S. PATENT DOCUMENTS

| | | | |
|---|---|---|---|
| 4,983,038 A | 1/1991 | Ohki et al. | |
| 5,469,251 A | 11/1995 | Kosaka et al. | |
| 2005/0148091 A1 | 7/2005 | Kitaguchi et al. | |
| 2006/0073076 A1 | 4/2006 | Ichiki et al. | |
| 2006/0194307 A1 | 8/2006 | Yasuda et al. | |
| 2010/0068824 A1 * | 3/2010 | Kimura ........................ | 436/501 |

FOREIGN PATENT DOCUMENTS

| | | |
|---|---|---|
| JP | 61182549 A | 8/1986 |
| JP | 63259466 A | 10/1988 |
| JP | 6426125 A | 1/1989 |
| JP | 02181632 A | 7/1990 |
| JP | 5346390 A | 12/1993 |
| JP | 10197440 A | 7/1998 |
| JP | 2002071658 A | 3/2002 |
| JP | 2003302330 A | 10/2003 |
| JP | 2004085323 A | 3/2004 |
| JP | 2005214691 A | 8/2005 |
| JP | 2006081406 A | 3/2006 |
| JP | 2006180810 A | 7/2006 |
| WO | 0113127 A1 | 2/2001 |

OTHER PUBLICATIONS

On-Chip Biotechnologies Co., Ltd, Feature Article (Introduction of Company Presenting in 7th International Bio Expo) Development of Compact Flow Cytometer Using Disposable Flow Cell Chip, English Translation of Experimental Medicine, Jul. 2008, pp. 1-4, vol. 26, No. 11.

* cited by examiner

*Primary Examiner* — Michael P Stafira
(74) *Attorney, Agent, or Firm* — Sughrue Mion, PLLC (57) ABSTRACT

An apparatus for measuring a particle in a liquid, the apparatus having a function that, using a flow channel into which a sample liquid containing a particle is introduced, a pair of flow channels into which a sheath liquid is introduced, the pair of the flow channels being arranged on the opposite sides of the flow channel and joined, and a flow channel in which these flow channels are joined and the sample liquid and the sheath liquid on the opposite sides of the sample liquid flow, applies laser light to a particle flowing in a flow channel in the flow cell, detects scattered light or fluorescence generated from the particle and analyzes the particle.

7 Claims, 5 Drawing Sheets

FLOW CYTOMETER AND FLOW CELL FOR THE SAME

BACKGROUND OF THE INVENTION

1. Field of the Invention

The present invention relates to a flow cytometer or a cell sorter for biological particles such as cells and/or bacteria. In particular, the present invention relates to an apparatus and a flow cell structure enabling use of a single-use flow cell.

2. Description of the Related Art

A flow cytometer is an apparatus in which a suspension containing particles such as fluorescence-labelled cells and/or bacteria is made to flow in a flow cell, the flow channel is irradiated with light, and scattered light and/or fluorescence generated when the particles pass through the irradiated region is measured, thereby quantifying the sizes of the particles and/or determining the kinds of the particles. Furthermore, a flow cytometer functions as a cell analysis unit for a cell sorter apparatus for sorting cells, etc., according to their kinds.

In a flow cytometer, a laser beam is narrowed down and applied to a flow channel in a flow cell. As the diameter of the beam is smaller, the energy density of the irradiation can be enhanced and the signal strength is thereby increased, enabling enhancement of the detection sensitivity. However, a large difference in signal strength occurs between particles passing through the central portion of the beam and particles passing through the peripheral portion of the beam. In order to prevent occurrence of this difference, it is necessary to perform either of the following: 1) widening of the laser beam to have a width larger than the width of the flow channel; and 2) high-speed sheath flows are provided around a sample flow to limit the portion of the flow channel where the particles pass through to be narrow. The former case has the drawback of the detection sensitivity being lowered as a result of a decrease in the energy density of the irradiation caused due to the widening of the beam. However, in this case, the sheath flows require an amount of liquid larger than that of the sample flow, and thus is conventionally connected to an external tank of several liters or more. Thus, conventionally, it is impossible to replace the entire liquid sending system. As described above, in a flow cytometer including a tank of a large capacity in its liquid sending system, it is impossible to readily replace the entire liquid sending system.

Therefore, methods for enabling use of a single-use flow cell have been proposed. Japanese Patent Laid-Open No. 2004-85323 discloses that a means using a flow caused by a gravity difference occurring due to the difference between surface levels of an introduced fluid for the flow rate of the fluid is provided to a flow cell chip, enabling the entire liquid sending system to be replaced by means of replacement of the chip. However, because of the gravity difference occurring due to a surface level difference of not more than around 1 cm in the chip, a high flow rate can not be provided, requiring one hour or more for measuring a minute sample of around 10 microliters. Japanese Patent Laid-Open No. 2003-302330 discloses a method for providing stable liquid sending by applying the same pressure to two sheath liquid ports and a sample liquid port on the upstream side. However, a problem arises in that where the surface levels of the two sheath liquids are different from each other, the balance of the sheath flows varies.

Where the flow cell to be used is made of quartz, it is not suitable for a single-use one because it is expensive. Meanwhile, methods for manufacturing a micro fluid chip made of a resin have been laid open. Japanese Patent Laid-Open No. 2006-81406 discloses a micro fluid device including a flow channel for polymerase chain reaction, the flow channel being formed by attaching a substrate resin film and an injection-molded resin member having a recess on a surface thereof to each other, or attaching the substrate resin film, a spacer resin film and another substrate resin film to one another in this order.

However, in the case of a flow cell for a flow cytometer in which a laser beam with a high energy density being used, a problem arises in that where an inexpensive transparent resin is used as a material for the flow cell, fluorescence from the material occurs even when visible light with a wavelength of 400 nm or more is applied, resulting in background noise light in fluorescence detection. The existence of this fluorescence causes deterioration of the fluorescence detection sensitivity of the flow cytometer. In the case of a flow cell made of glass, fluorescence occurs with a light having a wavelength shorter than 400 nm.

Furthermore, in an ordinary flow cytometer, a sample liquid is made to flow at a high speed together with a large amount of sheath flows, and thus, a sample liquid, once it is measured, is diluted by the sheath liquid and in addition, is contaminated by another sample liquid, and therefore, in general, the sample liquid is discarded. However, this is a great disadvantage when measuring a precious sample in a small amount.

Therefore, there is a demand for a single-use flow cell enabling easy replacement of a liquid sending system including sample liquid tanks and sheath liquid tanks, liquid sending pipes and a flow cell and not requiring cleansing for each sample replacement.

SUMMARY OF THE INVENTION

In view of the aforementioned circumstances, the present invention provides a flow cytometer apparatus and a flow cell, which use a single-use flow cell and enable replacement of the entire liquid sending system by means of mere replacement of the flow cell, and also enables collection of a sample free from contamination. In other words, the present invention provides an apparatus for measuring a particle in a liquid, and a flow cell below:

(1) An apparatus for measuring a particle in a liquid, the apparatus comprising: a stage with a flow cell mounted thereon, the flow cell including a first flow channel into which a sample liquid containing a particle is introduced, second and third flow channels into which a sheath liquid is introduced, the second and third flow channels being arranged on opposite sides of the first flow channel, and a fourth flow channel in which the first to third flow channels are joined, the first to fourth flow channels being formed on a substrate;

laser light application means for applying laser light to the particle flowing in the fourth flow channel; and means for detecting and analyzing scattered light or fluorescence generated from the particle, the flow cell further including:

fifth to seventh flow channels provided downstream of the fourth flow channel, the fifth to seventh flow channels being symmetrical to the first to third flow channels provided upstream of the fourth flow channel; and a first liquid storage tank and a second liquid storage tank provided upstream of the first to third flow channels and downstream of the fifth to seventh flow channels, respectively, wherein:

the second and third flow channels into which the sheath liquid is introduced are connected to the first liquid storage tank;

the first flow channel into which the sample liquid is introduced is connected to a third liquid storage tank provided inside the first liquid storage tank;

the second and third flow channels share a same liquid surface in the first liquid storage tank, the third liquid storage tank is independent from the first liquid storage tank and has a structure preventing the sheath liquid and the sample liquid from being mixed in the first liquid storage tank;

the fifth flow channel at the center of the downstream flow channels is connected to a fourth liquid storage tank provided inside the second liquid storage tank, and the sixth and seventh separated flow channels on opposite sides of the fifth flow channel are connected to the second liquid storage tank;

a gas with a constant pressure higher than an atmospheric pressure is introduced into the first liquid storage tank using a detachable cap structure, a flow rate of the sample liquid is controlled to be constant by controlling the pressure of the gas, the sample liquid is collected into the fourth liquid storage tank on the downstream side, and the sheath liquid is collected into the second liquid storage tank.

(2) An apparatus for measuring a particle in a liquid, the apparatus comprising: a stage with a flow cell mounted thereon, the flow cell including a first flow channel into which a sample liquid containing a particle is introduced, second and third flow channels into which a sheath liquid is introduced, the second and third flow channels being arranged on opposite sides of the first flow channel, and a fourth flow channel in which the first to third flow channels are joined, the first to fourth flow channels being formed on a substrate;

laser light application means for applying laser light to the particle flowing in the fourth flow channel; and means for detecting and analyzing scattered light or fluorescence generated from the particle, the flow cell further including:

fifth to seventh flow channels provided downstream of the fourth flow channel, the fifth to seventh flow channels being symmetrical to the first to third flow channels provided upstream of the fourth flow channel; and a first liquid storage tank and a second liquid storage tank provided upstream of the first to third flow channels and downstream of the fifth to seventh flow channels, respectively, wherein:

the second and third flow channels into which the sheath liquid is introduced are connected to the first liquid storage tank;

the first flow channel into which the sample liquid is introduced is connected to a third liquid storage tank provided inside the first liquid storage tank;

the second and third flow channels share a same liquid surface in the first liquid storage tank, the third liquid storage tank is independent from the first liquid storage tank and has a structure preventing the sheath liquid and the sample liquid from being mixed in the first liquid storage tank;

the fifth flow channel at the center of the downstream flow channels is connected to a fourth liquid storage tank provided inside the second liquid storage tank, and the sixth and seventh separated flow channels on opposite sides of the fifth flow channel are connected to the second liquid storage tank;

a gas with a constant pressure lower than an atmospheric pressure is introduced into the second liquid storage tank using a detachable cap structure, a flow rate of the sample liquid is controlled to be constant by controlling the pressure of the gas, the sample liquid is collected into the fourth liquid storage tank on the downstream side, and the sheath liquid is collected into the second liquid storage tank.

(3) A flow cell comprising: a first flow channel into which a sample liquid is introduced;

second and third flow channels into which a sheath liquid is introduced, the second and third flow channels being arranged on opposites sides of the first flow channel; and a fourth flow channel in which the first to third flow channels are joined, forming a flow of the sheath liquid on either side of a flow of the sample liquid, the first to fourth flow channels being provided on a substrate, wherein:

a pattern of the flow channels forms a structure in which the upstream side and the downstream side of the flow channels are symmetrical to each other;

a first liquid storage tank and a second liquid storage tank are provided on the upstream side and the downstream side of the flow cell, respectively; the second and third flow channels on the upstream side, into which the sheath liquid is introduced, are connected to the first liquid storage tank;

the first flow channel into which the sample liquid is introduced is connected to a third liquid storage tank provided inside the first liquid storage tank;

the sheath liquids connected to the second and third flow channels share a same liquid surface in the first liquid storage tank, and the third liquid storage tank is independent from the first liquid storage tank and has a structure preventing the sheath liquid and the sample liquid from being mixed in the first liquid storage tank;

the fourth flow channel in which the sheath liquid and the sample liquid are joined is divided on the downstream side in a pattern symmetrical to that on the upstream side, and a flow channel at the center of the downstream flow channels is connected to a fourth liquid storage tank in the second liquid storage tank, and separated flow channels on opposite sides of the center flow channel are connected to the second liquid storage tank.

(4) A flow cell according to (3) above, wherein a plurality of the flow channel pattern in the flow cell are formed in parallel on the substrate.

(5) A flow cell for measuring a particle in a liquid, the flow cell containing a resin, and making a sample liquid flow therein to measure fluorescence or scattered light in the sample liquid, wherein a part of a region of a substrate where a flow channel is formed, the part of the region being an irradiated region, has a thickness smaller than that of the remaining region of the substrate.

(6) A flow cell for measuring a particle in a liquid according to (3) or (4) above, wherein the flow cell contains a resin, and a part of the region of the substrate where the flow channels are formed, the part of the region being an irradiated region, has a thickness smaller than that of the remaining region of the substrate.

The present invention provides a high-sensitive flow cytometer enabling use of an inexpensive resin flow cell, and also enabling replacement of the entire liquid sending system by means of replacement of the flow cell. In other words, a high-sensitive flow cytometer using a single-use flow cell can be provided.

An apparatus and a flow cell for the same, which simultaneously fulfill the advantages of: 1) no need of cleansing a liquid sending system for each measurement; 2) enabling a sample liquid after measurement to be collected without being diluted and free from contamination; and 3) the flow cell being inexpensive are provided for a flow cytometer.

DESCRIPTION OF SYMBOLS

1 . . . flow cell substrate, 2 . . . flow channel in a flow cell, 3 . . . sample liquid, 4, 5 . . . liquid storage tank, 6 . . . sheath liquid, 7 . . . cap, 8 . . . pipe that guides a pressurized gas, 9 . . . pump, 10 and 11 . . . laser light source, 12 . . . condenser lens, 16,19,22 . . . dichroic mirror, 17 . . . beam stopper, 18 . . . photo diode, 21, 24, and 27 . . . photomultiplier tube, 20, 23 and 26 . . . band pass filter, 25 . . . mirror.

DESCRIPTION OF THE PREFERRED EMBODIMENTS

Hereinafter, embodiments of the present invention will be described; however, it should be understood that: the present invention is not limited to these specific examples; and many modifications and variations are possible without deviating from the spirit of the present invention.

Figure 1:
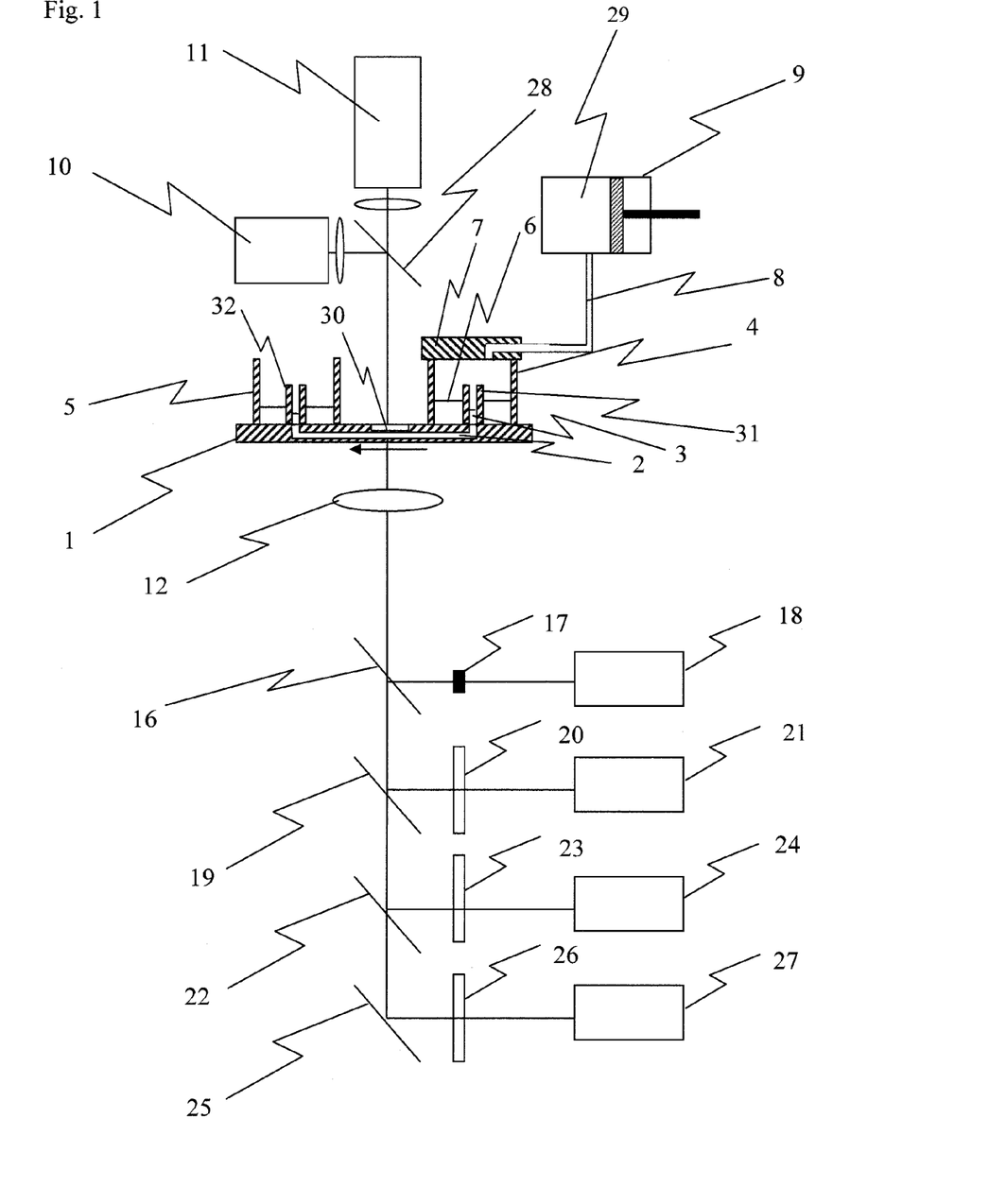
FIG. 1 is a schematic drawing illustrating a particle image measurement apparatus according to the present invention.

FIG. 1 is a schematic diagram illustrating a particle measurement apparatus according to the present invention. Reference numeral 1 denotes a flow cell-body substrate made of an acrylic transparent resin, in which a recessed flow channel pattern is formed on the back side of the substrate by means of injection molding, and a sheet with a thickness of approximately 100 um is attached to the flow channel pattern portion of the substrate, thereby forming a flow channel. A typical cross-section of the flow channel is 80 um wide and 25 um deep. Reference numeral 2 denotes a flow channel in which a sample liquid flows. Reference numeral 31 denotes a liquid storage tank for a sample liquid, reference numeral 4 shown at the portion surrounding the liquid storage tank 31 is a liquid storage tank 6 for a sheath liquid. The sample liquid is separated from the sheath liquid by means of a partition wall. The sheath liquid is connected to a pair of flow channels which are joined with the flow channel for the sample liquid 3 from the opposites sides of the flow channel for the sample liquid 3 (see FIG. 3). As shown in FIG. 1, the sheath liquids 6, which are connected to the pair of flow channels inside the liquid storage tank 4, share the same liquid surface. An air 29, which has been pressurized by a pump 9, is provided to the liquid storage tank 4 through a pipe 8 via a cap 7. The pressure value of the air is typically 2 to 20 kPa. Inside the liquid storage tank 4, the same air pressure is applied to the sheath liquid and the sample liquid, and the sheath liquids share the same liquid surface, and thus, an equal pressure is consistently applied to the pair of flow channels. Accordingly, the sample liquid flows gathering at the center of the flow channel by means of the sheath liquid flows on the opposite sides thereof (see FIG. 4). Since the flow channels on the downstream side has a pattern symmetrical to the flow channel pattern on the upstream side, after passing through a laser irradiated region 34 (see FIG. 4), the liquid is separated again into the sample liquid and the sheath liquid by means of branch flow channels on the downstream side. The center branch flow channel from which the separated sample liquid is collected is connected to a liquid storage tank 32, and the pair of branch flow channels on the opposite sides of the center branch flow channel, from which the sheath flows are collected is connected to a liquid storage tank 5 (see also FIG. 3). Reference numerals 10 and 11 in FIG. 1 denote laser light sources for laser light with a wavelength of 473 nm and laser light with a wavelength of 640 nm, respectively. Laser light beams emitted from these light sources are adjusted to be on the substantially same axis using a dichroic mirror 28 and applied to the flow channel in the flow cell substrate 1. Scattered light and fluorescence generated when particles flowing in the flow channel passed through the light beam are collected by a lens 12, and light of 473 nm is reflected by a dichroic mirror 16, direct transmitted light is removed by a beam stopper 17, and scattered light is detected by a photo diode 18. Short-wavelength light with a wavelength range of no more than 550 nm is reflected by a dichroic mirror 19, light of 510 to 550 nm is transmitted by a band pass filter 20, and fluorescence is detected by a photomultiplier tube 21. Short-wavelength light with wavelengths of less than 750 nm is reflected by a dichroic mirror 22, light of 680 to 720 nm is transmitted by a band pass filter 23, and fluorescence is detected by a photomultiplier tube 24. Long-wavelength light with a wavelength range of no less than 750 nm is reflected by a mirror 25 and transmitted by a band pass filter 26, and fluorescence is detected by a photomultiplier tube 27. As described above, scattered light and fluorescence from the particles are detected and recorded for each particle whose signal strength magnitude has been detected.

Figure 2:
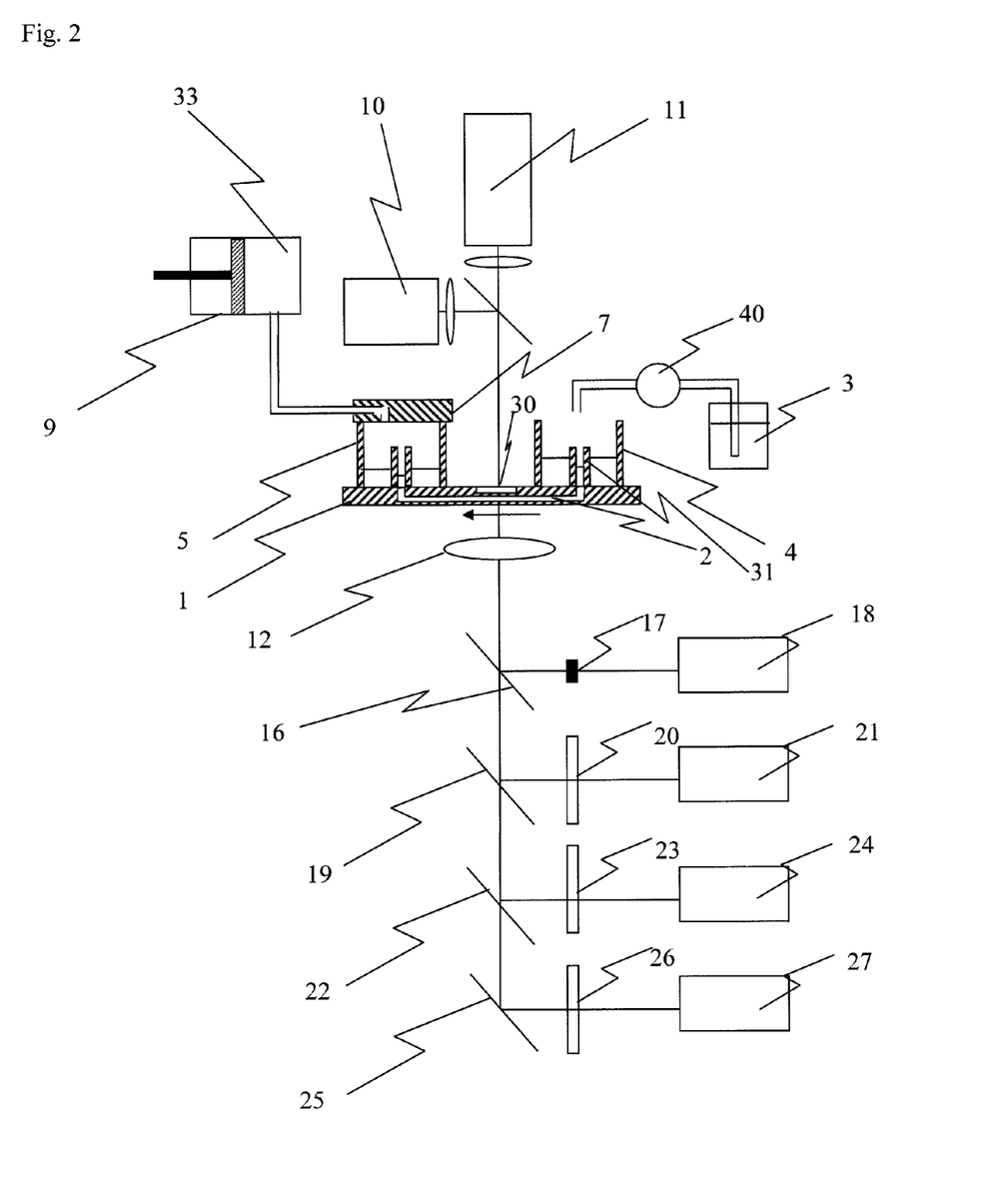
FIG. 2 is a schematic drawing illustrating another particle image measurement apparatus according to the present invention.

FIG. 2 is a schematic diagram illustrating a particle measurement apparatus according to another embodiment of the present invention. The apparatus shown in FIG. 2 is different from the embodiment shown in FIG. 1 in that an air 33 with a constant pressure lower than that of an atmosphere is provided by providing a cap to a liquid storage tank 5 on the downstream side. In a liquid storage tank 4 on the upstream side of the flow cell, a sample liquid 3 is contactlessly supplied to a liquid storage tank 31 by means of dripping using liquid sending performed by a metering pump. As a result of sending a sample liquid by applying a negative pressure to the liquid storage tank on the downstream side as described above, a larger amount of sample liquid can be sent for a long period of time for measurement.

The thickness of the part of the material (substrate) of a flow cell according to the present invention where laser light passes through is smaller than that of the part around the laser light passing part of the flow cell in order to reduce autofluorescence of the flow cell. A region 30 in FIGS. 1 and 2 is a region in which the thickness of the flow cell is smaller than that of the remaining region. For example, the remaining region is 1.5 mm thick while the region is 0.5 mm thick or less.

Figure 3:
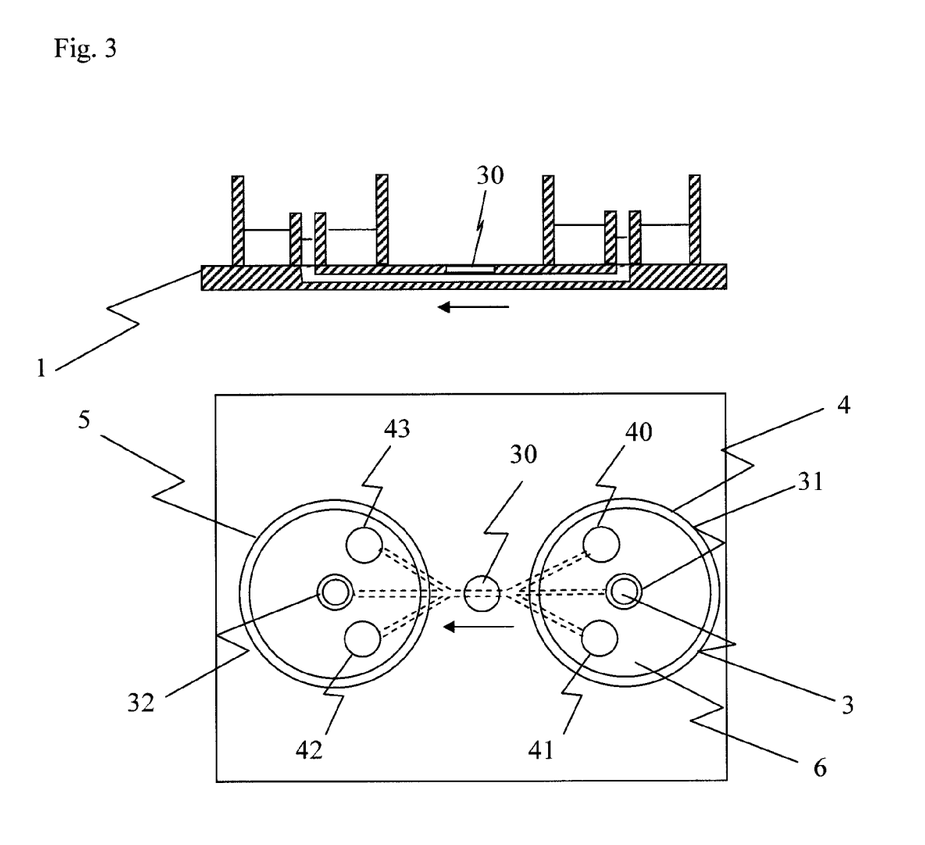
FIG. 3 is a schematic drawing of a flow cell according to the present invention.

FIG. 3 is a schematic diagram of a flow cell according to the present invention. The panel shown in the lower part of FIG. 3 shows a plan view of the flow cell. A sheath liquid 6 is introduced to flow channels from openings 40 and 41, and joined with a sample liquid 3 from a liquid storage tank 31 for a sample at a downstream portion. The joined liquids pass through the flow channel including the region 30 and separated again into respective flow channels at a further downstream portion, and the sample liquid 3 passes through the center flow channel and stored in a liquid storage tank 32, and the sheath liquid flows in flow channels on the opposite sides of the center flow channel and discharged from openings 42 and 43 into a liquid storage tank 5. The flow channel in the region 30 is set to be a laser irradiated region. A recess is formed on the side of the flow cell substrate opposite the side on which the flow channel pattern is formed, and the thickness totaling the thickness of the substrate, the depth of the flow channel and the thickness of the sheet in that region is made to be smaller than the thickness of the remaining region (for example, 1.5 mm), for example, 0.5 mm or less. As a result, auto-fluorescence of the flow cell caused by 473 nm laser irradiation has been reduced to approximately one third compared to the case where the part has the same thickness as that of the remaining region (for example, 1.5 mm thick).

Figure 4:
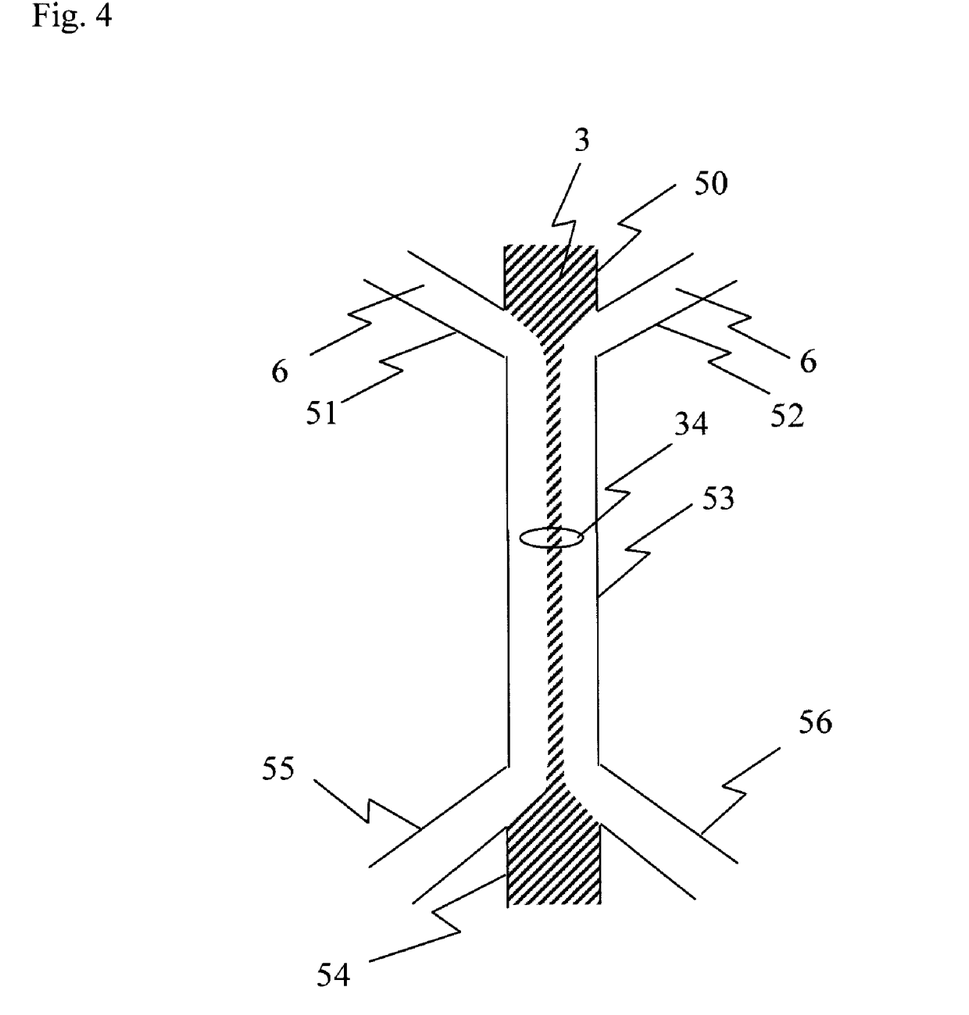
FIG. 4 is a schematic drawing illustrating a flow of a sample liquid in a flow channel inside a flow cell according to the present invention.

FIG. 4 is a schematic diagram illustrating the flow of a sample liquid in a flow channel inside a flow cell according to the present invention. Reference numeral 34 in FIG. 4 denotes a laser irradiated region in the flow channel. A flow channel 50 in which the sample liquid 3 from the sample storage tank 31 flows is joined with flow channels 51 and 52 in which the sheath liquid 6 from the liquid storage tank 4 flows, thereby forming a flow channel 53. The flow channel 53 are separated again at a downstream portion into a flow channel 54 in which the sample liquid 3 flows and flow channels 55 and 56 in which the sheath liquid 6 flows.

Figure 5:
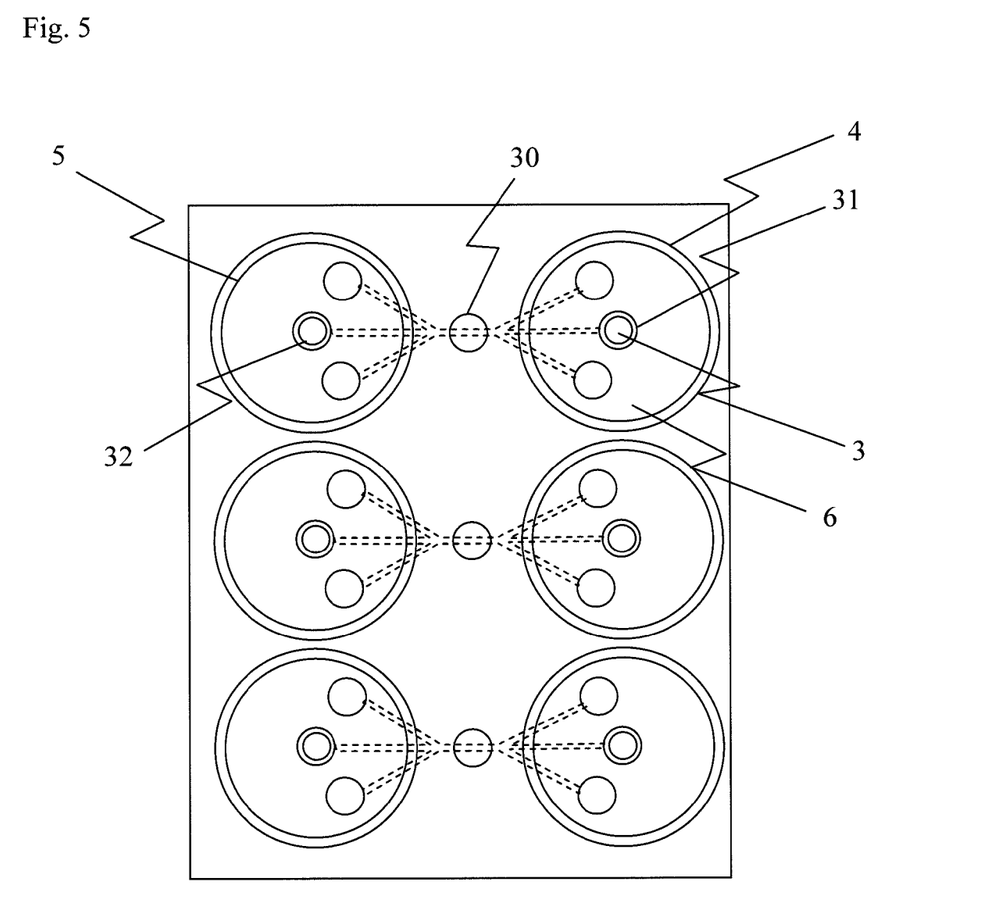
FIG. 5 is a schematic drawing illustrating another flow cell according to the present invention.

FIG. 5 is a schematic diagram illustrating another embodiment of a flow cell according to the present invention, in which a plurality of the flow channel pattern shown in FIG. 3 are formed on a substrate. Formation of a plurality of flow cell patterns on a single substrate as shown in the Figure enables enhancement of the measurement throughput.

Industrial Applicability

The present invention is useful as a high-sensitive flow cytometer employing a single-use flow cell.

What is claimed is:

1. An apparatus for measuring a particle in a liquid, the apparatus comprising: a stage with a flow cell mounted thereon, the flow cell including a first flow channel into which a sample liquid containing a particle is introduced, second and third flow channels into which a sheath liquid is introduced, the second and third flow channels being arranged on opposite sides of the first flow channel, and a fourth flow channel in which the first to third flow channels are joined, the first to fourth flow channels being formed on a substrate;

laser light application means for applying laser light to the particle flowing in the fourth flow channel; and means for detecting and analyzing scattered light or fluorescence generated from the particle, the flow cell further including:

fifth to seventh flow channels provided downstream of the fourth flow channel, the fifth to seventh flow channels being symmetrical to the first to third flow channels provided upstream of the fourth flow channel; and a first liquid storage tank and a second liquid storage tank provided upstream of the first to third flow channels and downstream of the fifth to seventh flow channels, respectively, wherein:

the second and third flow channels into which the sheath liquid is introduced are connected to the first liquid storage tank;

the first flow channel into which the sample liquid is introduced is connected to a third liquid storage tank provided inside the first liquid storage tank;

the second and third flow channels share a same liquid surface in the first liquid storage tank, the third liquid storage tank is independent from the first liquid storage tank and has a structure preventing the sheath liquid and the sample liquid from being mixed in the first liquid storage tank;

the fifth flow channel at the center of the downstream flow channels is connected to a fourth liquid storage tank provided inside the second liquid storage tank, and the sixth and seventh separated flow channels on opposite sides of the fifth flow channel are connected to the second liquid storage tank;

a gas with a constant pressure higher than an atmospheric pressure is introduced into the first liquid storage tank using a detachable cap structure, a flow rate of the sample liquid is controlled to be constant by controlling the pressure of the gas, the sample liquid is collected into the fourth liquid storage tank on the downstream side, and the sheath liquid is collected into the second liquid storage tank.

2. An apparatus for measuring a particle in a liquid, the apparatus comprising: a stage with a flow cell mounted thereon, the flow cell including a first flow channel into which a sample liquid containing a particle is introduced, second and third flow channels into which a sheath liquid is introduced, the second and third flow channels being arranged on opposite sides of the first flow channel, and a fourth flow channel in which the first to third flow channels are joined, the first to fourth flow channels being formed on a substrate;

laser light application means for applying laser light to the particle flowing in the fourth flow channel; and means for detecting and analyzing scattered light or fluorescence generated from the particle, the flow cell further including:

fifth to seventh flow channels provided downstream of the fourth flow channel, the fifth to seventh flow channels being symmetrical to the first to third flow channels provided upstream of the fourth flow channel; and a first liquid storage tank and a second liquid storage tank provided upstream of the first to third flow channels and downstream of the fifth to seventh flow channels, respectively, wherein:

the second and third flow channels into which the sheath liquid is introduced are connected to the first liquid storage tank;

the first flow channel into which the sample liquid is introduced is connected to a third liquid storage tank provided inside the first liquid storage tank;

the second and third flow channels share a same liquid surface in the first liquid storage tank, the third liquid storage tank is independent from the first liquid storage tank and has a structure preventing the sheath liquid and the sample liquid from being mixed in the first liquid storage tank;

the fifth flow channel at the center of the downstream flow channels is connected to a fourth liquid storage tank provided inside the second liquid storage tank, and the sixth and seventh separated flow channels on opposite sides of the fifth flow channel are connected to the second liquid storage tank;

a gas with a constant pressure lower than an atmospheric pressure is introduced into the second liquid storage tank using a detachable cap structure, a flow rate of the sample liquid is controlled to be constant by controlling the pressure of the gas, the sample liquid is collected into the fourth liquid storage tank on the downstream side, and the sheath liquid is collected into the second liquid storage tank.

3. A flow cell comprising: a first flow channel into which a sample liquid is introduced;

second and third flow channels into which a sheath liquid is introduced, the second and third flow channels being arranged on opposites sides of the first flow channel; and a fourth flow channel in which the first to third flow channels are joined, forming a flow of the sheath liquid on either side of a flow of the sample liquid, the first to fourth flow channels being provided on a substrate, wherein:

a pattern of the flow channels forms a structure in which the upstream side and the downstream side of the flow channels are symmetrical to each other;

a first liquid storage tank and a second liquid storage tank are provided on the upstream side and the downstream side of the flow cell, respectively;

the second and third flow channels on the upstream side, into which the sheath liquid is introduced, are connected to the first liquid storage tank;

the first flow channel into which the sample liquid is introduced is connected to a third liquid storage tank provided inside the first liquid storage tank;

the sheath liquids connected to the second and third flow channels share a same liquid surface in the first liquid storage tank, and the third liquid storage tank is independent from the first liquid storage tank and has a structure preventing the sheath liquid and the sample liquid from being mixed in the first liquid storage tank;

the fourth flow channel in which the sheath liquid and the sample liquid are joined is divided on the downstream side in a pattern symmetrical to that on the upstream side, and a flow channel at the center of the downstream flow channels is connected to a fourth liquid storage tank in the second liquid storage tank, and separated flow channels on opposite sides of the center flow channel are connected to the second liquid storage tank.

4. The flow cell according to claim 3, wherein a plurality of the flow channel pattern in the flow cell are formed in parallel on the substrate.

5. The flow cell for measuring a particle in a liquid according to claim 3 or 4, wherein the flow cell contains a resin, and a part of the region of the substrate where the flow channels are formed, the part of the region being an irradiated region, has a thickness smaller than that of the remaining region of the substrate.

6. An apparatus for measuring a particle in a liquid, the apparatus comprising:

a stage with a flow cell mounted thereon, the flow cell including a first flow channel into which a sample liquid containing a particle is introduced, second and third flow channels into which a sheath liquid is introduced, the second and third flow channels being arranged on opposite sides of the first flow channel, and a fourth flow channel in which the first to third flow channels are joined, the first to fourth flow channels being formed on a substrate;

a laser light application means for applying a laser light to the particle flowing in the fourth flow channel; and a means for detecting and analyzing scattered light or fluorescence generated from the particle, wherein:

the second and third flow channels into which the sheath liquid is introduced are connected to a first liquid storage tank;

the first flow channel into which the sample liquid is introduced is connected to a third liquid storage tank provided inside the first liquid storage tank;

the sample liquid in the third liquid storage tank is separated from the sheath liquid in the first liquid storage tank by means of a boundary wall higher than the substrate surface, the downstream end of the fourth flow channel is connected to the second liquid storage tank which is opened to the atmosphere, and the first liquid storage tank is pressurized by a gas of two to twenty kPa, which is higher than the atmospheric pressure, so that the flow rate of the sample liquid and a flow rate of the sheath liquid on both sides are controlled by the same pressure.

7. An apparatus for measuring a particle in a liquid, the apparatus comprising: a stage with a flow cell mounted thereon, the flow cell including a first flow channel into which a sample liquid containing a particle is introduced, second and third flow channels into which a sheath liquid is introduced, the second and third flow channels being arranged on opposite sides of the first flow channel, and a fourth flow channel in which the first to third flow channels are joined, the first to fourth flow channels being formed on a substrate;

laser light application means for applying laser light to the particle flowing in the fourth flow channel; and means for detecting and analyzing scattered light or fluorescence generated from the particle, wherein:

the second and third flow channels into which the sheath liquid is introduced are connected to a first liquid storage tank;

the first flow channel into which the sample liquid is introduced is connected to a third liquid storage tank provided inside the first liquid storage tank;

the sample liquid in the third liquid storage tank is separated from the sheath liquid in the first liquid storage tank by means of a boundary wall higher than the substrate surface, the upstream end of the fourth flow channel is connected to the first liquid storage tank which is opened to the atmosphere, and the second liquid storage tank is pressurized by a gas lower than the atmospheric pressure, so that the flow rate of the sample liquid and the flow rate of the sheath liquid on both sides are controlled by the same pressure.

* * * * *